(12) United States Patent
Jeon et al.

(10) Patent No.: US 10,975,003 B2
(45) Date of Patent: Apr. 13, 2021

(54) N-HEPTANE PRODUCTION METHOD

(71) Applicants: SK Innovation Co., Ltd., Seoul (KR); SK Global Chemical Co., Ltd., Seoul (KR)

(72) Inventors: Kyung Jin Jeon, Daejeon (KR); Soo Kil Kang, Daejeon (KR)

(73) Assignees: SK Innovation Co., Ltd., Seoul (KR); SK Global Chemical Co., Ltd., Seoul (KR)

(*) Notice: Subject to any disclaimer, the term of this patent is extended or adjusted under 35 U.S.C. 154(b) by 0 days.

(21) Appl. No.: 16/850,158

(22) Filed: Apr. 16, 2020

(65) Prior Publication Data

US 2020/0361837 A1 Nov. 19, 2020

(30) Foreign Application Priority Data

May 13, 2019 (KR) .................. 10-2019-0055404

(51) Int. Cl.
| | |
|---|---|
| C07C 5/03 | (2006.01) |
| C07C 7/00 | (2006.01) |
| C07C 7/04 | (2006.01) |
| C07C 7/10 | (2006.01) |
| C07C 9/15 | (2006.01) |
| C10G 21/14 | (2006.01) |
| C10G 69/02 | (2006.01) |

(Continued)

(52) U.S. Cl.
CPC ............. *C07C 5/03* (2013.01); *C07C 7/005* (2013.01); *C07C 7/04* (2013.01); *C07C 7/10* (2013.01); *C07C 9/15* (2013.01); *C10G 21/14* (2013.01); *C10G 69/02* (2013.01); *C10G 7/00* (2013.01); *C10G 21/00* (2013.01); *C10G 69/00* (2013.01); *C10G 2300/1044* (2013.01)

(58) Field of Classification Search
CPC ...... C07C 5/03; C07C 7/10; C07C 9/15; C07C 7/005; C07C 7/04; C10G 69/02; C10G 21/14; C10G 7/00; C10G 21/00; C10G 69/00; C10G 2300/1044

See application file for complete search history.

(56) References Cited

U.S. PATENT DOCUMENTS 3,732,325 A 5/1973 Pharis et al.

FOREIGN PATENT DOCUMENTS

| KR | 101192057 B1 | 10/2002 | |
|---|---|---|---|
| KR | 101699632 B1 * | 1/2017 | ............... C07C 7/04 |

(Continued)

*Primary Examiner* — Ali Z Fadhel
(74) *Attorney, Agent, or Firm* — The Webb Law Firm (57) ABSTRACT

Provided is an n-heptane production method including: a step of distilling a feed containing C6–, C7, and C8+ hydrocarbon components, removing the C8+ and C6– hydrocarbon components, and separating the C7 hydrocarbon component; a step of adding the separated C7 hydrocarbon component to a hydrogenation apparatus and hydrogenating the separated C7 hydrocarbon component; a step of adding the hydrogenated C7 hydrocarbon component to a simulated moving bed (SMB) apparatus and separating the hydrogenated C7 hydrocarbon component into an extract containing n-heptane and a raffinate containing other components; and a step of distilling the extract and separating the n-heptane in an extract column, wherein a purity of the produced n-heptane is 98 wt % or higher.

5 Claims, 4 Drawing Sheets

(51) Int. Cl.
*C10G 7/00* (2006.01)
*C10G 21/00* (2006.01)
*C10G 69/00* (2006.01)

(56) References Cited

FOREIGN PATENT DOCUMENTS

| | | |
|---|---|---|
| KR | 101699632 B1 | 1/2017 |
| KR | 1020170081821 A | 7/2017 |
| KR | 101770907 B1 | 8/2017 |

\* cited by examiner

N-HEPTANE PRODUCTION METHOD

CROSS-REFERENCE TO RELATED APPLICATION

This application claims priority to Korean Patent Application No. 10-2019-0055404 filed May 13, 2019, the disclosure of which is hereby incorporated by reference in its entirety.

BACKGROUND OF THE INVENTION

Field of the Invention

The following disclosure relates to an n-heptane production method.

Description of Related Art

N-heptane with a purity of 99 wt % or higher is a high-value solvent product used as a pharmaceutical ingredient extract and a solvent used in a coating process for a display such as an organic light-emitting diode (OLED) display, a styrene butadiene rubber (SBR) polymerization process, and the like.

In addition, n-heptane with a purity of 99.8 wt % or higher is used for a reference fuel used in a measurement test of an octane number of gasoline, an analysis apparatus for high-performance liquid chromatography (HPLC), and a solvent used in pharmaceutical manufacture, and a product thereof is marketed separately from an n-heptane product with a purity of 99 wt % or higher.

An aromatic compound treatment process (a benzene, toluene, and xylene (BTX) process) that is a petrochemical process is a process of producing benzene, toluene, and xylene from naphtha subjected to a desulfurization process. N-paraffin is mixed with the desulfurized naphtha which is a raw material used in the BTX process.

Such an n-paraffin is commercially valuable by itself for the use as described above, and is advantageous in the aromatic compound treatment process due to the fact that a yield of the aromatic compound is increased after the n-paraffin component is removed.

Therefore, in a case where desulfurized naphtha is subjected to an removal of n-paraffin or a conversion of a component contained therein into a high-value n-paraffin component, and then the desulfurized naphtha is used as a raw material in the aromatic compound treatment process, yield ability in the entire process may be significantly increased.

SUMMARY OF THE INVENTION

An embodiment of the present invention is directed to providing an n-heptane production method capable of preventing a trade-off between an increase in purity and a decrease in production, while being capable of producing n-heptane with a high purity and furthermore producing n-heptane with an ultra-high purity of 99.8 wt % or higher from desulfurized naphtha.

In one aspect, an n-heptane production method includes: a step of distilling a feed containing C6−, C7, and C8+ hydrocarbon components, removing the C8+ and C6− hydrocarbon components, and separating the C7 hydrocarbon component; a step of adding the separated C7 hydrocarbon component to a hydrogenation apparatus and hydrogenating the separated C7 hydrocarbon component; a step of adding the hydrogenated C7 hydrocarbon component to a simulated moving bed (SMB) apparatus and separating the hydrogenated C7 hydrocarbon component into an extract containing n-heptane and a raffinate containing other components; and a step of distilling the extract and separating the n-heptane in an extract column, wherein a purity of the produced n-heptane is 98 wt % or higher.

The n-heptane production method may further include a step of recirculating a portion of the n-heptane separated in the extract column to a front end of the SMB apparatus.

More specifically, the n-heptane production method may further include a step of recirculating a portion of the n-heptane separated in the extract column between a rear end of the hydrogenation apparatus and a front end of the SMB apparatus.

In the recirculation step, a recirculation rate may be 30% to 60%.

More specifically, a purity of the produced n-heptane may be 99.8 wt % or higher.

The step of distilling the feed containing C6−, C7, and C8+ hydrocarbon components, removing the C8+ and C6− hydrocarbon components, and separating the C7 hydrocarbon component may include: a step of performing distillation and removing the C8+ hydrocarbon component in a first distillation column; and a step of performing distillation and removing the C6− hydrocarbon component in a second distillation column.

The step of distilling the feed containing C6−, C7, and C8+ hydrocarbon components, removing the C8+ and C6− hydrocarbon components, and separating the C7 hydrocarbon component may include: a step of performing distillation and removing the C6− hydrocarbon component in a first distillation column; and a step of performing distillation and removing the C8+ hydrocarbon component in a second distillation column.

The feed containing C6−, C7, and C8+ hydrocarbon components may be desulfurized naphtha.

The feed containing C6−, C7, and C8+ hydrocarbon components may contain, with respect to a total weight of 100 wt % thereof, 3 wt % to 10 wt % of C6− n-paraffin, 5 wt % to 15 wt % of C7 n-paraffin, 5 wt % to 20 wt % of C8+ n-paraffin, and a balance containing naphthene, isoparaffin, and an aromatic component.

In another general aspect, n-heptane produced by the n-heptane production method is provided.

Other features and aspects will be apparent from the following detailed description, the drawings, and the claims.

DETAILED DESCRIPTION OF MAIN ELEMENTS

10: First distillation column
11: Second distillation column
20: Hydrogenation apparatus 30: Third distillation column
40: Stripping apparatus
50: Simulated moving bed apparatus
51: Extract column
52: Raffinate column
53: Desorbent reservoir
60: Dryer
101: Recirculation pipe

DESCRIPTION OF THE INVENTION

Unless otherwise defined, all terms (including technical and scientific terms) used in the present specification have the same meanings as commonly understood by those skilled in the art to which the present invention pertains. Throughout the present specification, unless explicitly described to the contrary, "comprising" any components will be understood to imply the inclusion of other components rather than the exclusion of any other components. In addition, unless the context clearly indicates otherwise, a singular form includes a plural form.

Unless otherwise particularly defined in the present specification, the term "high purity n-heptane" may refer to n-heptane with a purity of 98 wt % or higher, and more specifically, 99 wt % or higher.

Unless otherwise particularly defined in the present specification, the term "ultra-high purity n-heptane" may refer to n-heptane with a purity of 99.8 wt % or higher.

The present invention relates to an n-heptane production method from desulfurized naphtha.

Specifically, according to the n-heptane production method according to an exemplary embodiment of the present invention, it is possible to produce a high purity n-heptane used as a pharmaceutical ingredient extract and a solvent used in a coating process for a display such as an organic light-emitting diode (OLED) display, a styrene butadiene rubber (SBR) polymerization process, and the like.

Furthermore, according to the n-heptane production method according to an exemplary embodiment of the present invention, it is possible to produce n-heptane with an ultra-high purity 99.8 wt % or higher with a high yield, the ultra-high purity n-heptane being capable of being used for a reference fuel used in a measurement test of an octane number, an analysis apparatus for high-performance liquid chromatography (HPLC), and a solvent used in pharmaceutical manufacture.

The n-heptane production method according to an exemplary embodiment of the present invention includes: a step of distilling a feed containing C6−, C7, and C8+ hydrocarbon components, removing the C8+ and C6− hydrocarbon components, and separating the C7 hydrocarbon component; a step of adding the separated C7 hydrocarbon component to a hydrogenation apparatus and hydrogenating the separated C7 hydrocarbon component; a step of adding the hydrogenated C7 hydrocarbon component to a simulated moving bed (SMB) apparatus and separating the hydrogenated C7 hydrocarbon component into an extract containing n-heptane and a raffinate containing other components; and a step of distilling the extract and separating the n-heptane in an extract column.

The n-heptane production method according to an exemplary embodiment of the present invention is an n-heptane production method from a feed containing C6−, C7, and C8+ hydrocarbon components. In the n-heptane production method, after separating only the C7 hydrocarbon component, hydrogenation and an SMB process may be sequentially performed.

The hydrogenation and the SMB process are sequentially performed on the feed, such that it is possible to produce n-heptane with a high purity of 98 wt % or higher, and more specifically, 99 wt % or higher, with a high yield.

In addition, n-heptane is produced by previously removing an aromatic component and the like through the hydrogenation and performing the SMB process only on non-aromatic components, such that it is possible to produce n-heptane while changing detailed conditions of the SMB process without consideration of a specific property of the aromatic component and the like, and it is possible to produce a high purity n-heptane without an additional distillation process after performing the SMB process.

Therefore, the process not only may be very easily operated and managed, but also may be simplified, which may reduce the cost of the entire process.

Specifically, in a case where the hydrogenation is performed after performing the SMB process, an aromatic component is inevitably mixed with the extract containing a large amount of n-heptane, which is a desired product, in the SMB process, which reduces an operational efficiency of the SMB process. Accordingly, it is required to set a condition of the SMB process in order to minimize the reduction of the operational efficiency, and to add a separation process such as an additional distillation process because the purity of the n-heptane is not sufficiently increased due to a large amount of residual components other than the n-heptane even after the hydrogenation is performed, and removal of hydrogenated products of the aromatic compound that have properties different from those of the n-heptane is necessarily performed.

On the other hand, in a case where the hydrogenation is previously performed, the aromatic component is removed in advance, and thus the aromatic component is not present in the extract in the subsequent SMB process. Therefore, the SMB process may be easily operated, and it is possible to produce a high purity n-heptane without an additional separation process after the hydrogenation is performed.

The n-heptane production method according to an exemplary embodiment of the present invention may further include a step of recirculating a portion of the n-heptane separated in the extract column to a front end of the SMB apparatus.

By further including the recirculation step, it is possible to produce n-heptane with an ultra-high purity of 99.8 wt % or higher with a high yield.

Specifically, in the n-heptane production method according to an exemplary embodiment of the present invention, in order to increase the purity of the n-heptane to 99.8 wt % or higher, it is required to increase the purity of the n-heptane in the feed added to the SMB process.

However, in order to increase the purity of the n-heptane in the feed added to the SMB process without recirculation, processing capacities in the previous processes are necessarily reduced, and the processing capacity in the SMB process is thus reduced. Therefore, production of n-heptane with a purity of 99.8 wt % or higher is decreased to the extent that the n-heptane is not industrially applicable in practice.

That is, since the purity of the n-heptane in the feed added to the SMB process and the processing capacity in the SMB process are in a trade-off relationship, there is a need for a solution for solving such a trade-off relationship.

To this end, the n-heptane production method according to an exemplary embodiment of the present invention may further include a step of recirculating a portion of the n-heptane separated in the extract column to a front end of the SMB apparatus.

That is, the portion of the n-heptane separated in the extract column after the SMB process is recirculated to the front end of the SMB apparatus, such that the purity of the n-heptane in the feed added to the SMB process may be increased. As a result, a purity of a final n-heptane product may be increased without reduction in the processing capacities in the entire process.

More specifically, the n-heptane production method according to an exemplary embodiment of the present invention may further include a step of recirculating a portion of the n-heptane separated in the extract column between a rear end of the hydrogenation apparatus and a front end of the SMB apparatus.

It may be more advantageous that the portion of the n-heptane separated in the extract column is recirculated between the rear end of the hydrogenation apparatus and the front end of the SMB apparatus.

This results from the fact that, in a case where the portion of the n-heptane is recirculated to a front end of the hydrogenation apparatus, as the processing capacities between the hydrogenation process and the SMB process are increased, the amount to be processed in a separation process such as a distillation process and a stripping process is increased between the hydrogenation process and the SMB process, and thus the cost of the process may be unnecessarily increased.

Meanwhile, in the recirculation step, a recirculation rate may be 30% to 60%, and more specifically, 35% to 55%. In order to produce a product while maintaining processing capacities in the processes at a predetermined level or higher, the recirculation rate is required to be maintained at an adequate level. When the recirculation rate is low, as the processing capacities in the processes are reduced, the production of the n-heptane may be decreased.

Within this range, the portion of the n-heptane separated in the extract column is recirculated to the front end of the SMB apparatus, such that it is possible to produce n-heptane with an ultra-high purity of 99.8 wt % or higher without reduction in processing capacities in the entire process.

Here, the recirculation rate may refer to the amount of n-heptane recirculated with respect to a total weight of 100 wt % of a discharge containing the n-heptane discharged from the extract column.

In the n-heptane production method according to an exemplary embodiment of the present invention, the feed containing C6−, C7, and C8+ hydrocarbon components may be desulfurized naphtha.

That is, the feed containing C6−, C7, and C8+ hydrocarbon components may be desulfurized naphtha obtained by performing a desulfurization process on naphtha separated from crude oil.

The desulfurized naphtha may contain, with respect to a total weight of 100 wt % thereof, 3 wt % to 10 wt % of C6− n-paraffin, 5 wt % to 15 wt % of C7 n-paraffin, 5 wt % to 20 wt % of C8+ n-paraffin, and a balance containing naphthene, isoparaffin, and an aromatic component.

More specifically, the desulfurized naphtha may contain, with respect to a total weight of 100 wt % thereof, 3 wt % to 10 wt % of C6− n-paraffin, 5 wt % to 15 wt % of C7 n-paraffin, 5 wt % to 20 wt % of C8+ n-paraffin, 20 wt % to 35 wt % of naphthene, 25 wt % to 40 wt % of isoparaffin, and 5 wt % to 15 wt % of an aromatic component.

In the n-heptane production method according to an exemplary embodiment of the present invention, the step of distilling the feed containing C6−, C7, and C8+ hydrocarbon components, removing the C8+ and C6− hydrocarbon components, and separating the C7 hydrocarbon component may include: a step of performing distillation and removing the C8+ hydrocarbon component in a first distillation column; and a step of performing distillation and removing the C6− hydrocarbon component in a second distillation column.

The C6− and C8+ hydrocarbon components may be removed from the feed containing C6−, C7, and C8+ hydrocarbon components through the distillation. In this case, the order of removing the C6− and C8+ hydrocarbon components is not limited to a specific order.

That is, the terms of the first distillation column and the second distillation column are given merely for convenience, and the number does not mean the order. After the C6− hydrocarbon component is removed, the C8+ hydrocarbon component may be removed. Alternatively, after the C8+ hydrocarbon component is removed, the C6− hydrocarbon component may be removed.

In the n-heptane production method according to an exemplary embodiment of the present invention, the distillation may be performed by a distillation method commonly known, and the number of stages of the distillation column may be adjusted as needed. As a non-limiting example, a single or plurality of distillation columns including a bottom reboiler and an overhead condenser and having the number of stages of 10 to 100 may be used.

In the n-heptane production method according to an exemplary embodiment of the present invention, the hydrogenation may be performed by a process of hydrogenating unsaturated hydrocarbons such as an aromatic component and an olefin into saturated hydrocarbons. Since, when a reactant is injected to a hydrogenation reactor, a temperature of the reactor and an outlet temperature are likely to increase due to reaction heat generated during the hydrogenation, it is preferable that the reactant to be added is injected to the hydrogenation reactor after lowering a temperature thereof. A specific hydrogenation method may be performed by a method known in the art, and is not limited to a specific method.

In the n-heptane production method according to an exemplary embodiment of the present invention, the SMB process using the SMB apparatus may be performed by a method in which a component having a high selectivity to an adsorbent is adsorbed to the adsorbent and is extracted as an extract, and residual components are discharged as a raffinate, using an apparatus including an adsorption bed with which a zeolite-based adsorbent is filled and an on-off valve. However, the present invention is not necessarily limited thereto.

Figure 1:
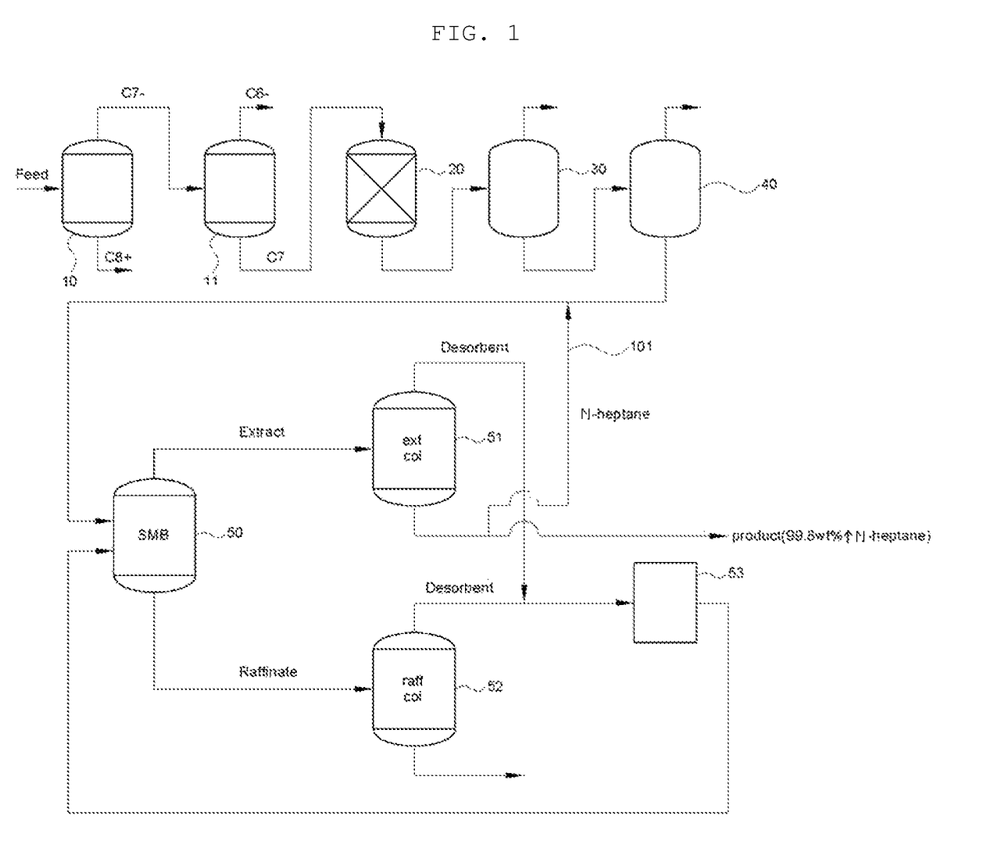
FIG. 1 is a process diagram of an n-heptane production method according to an exemplary embodiment of the present invention.
Figure 2:
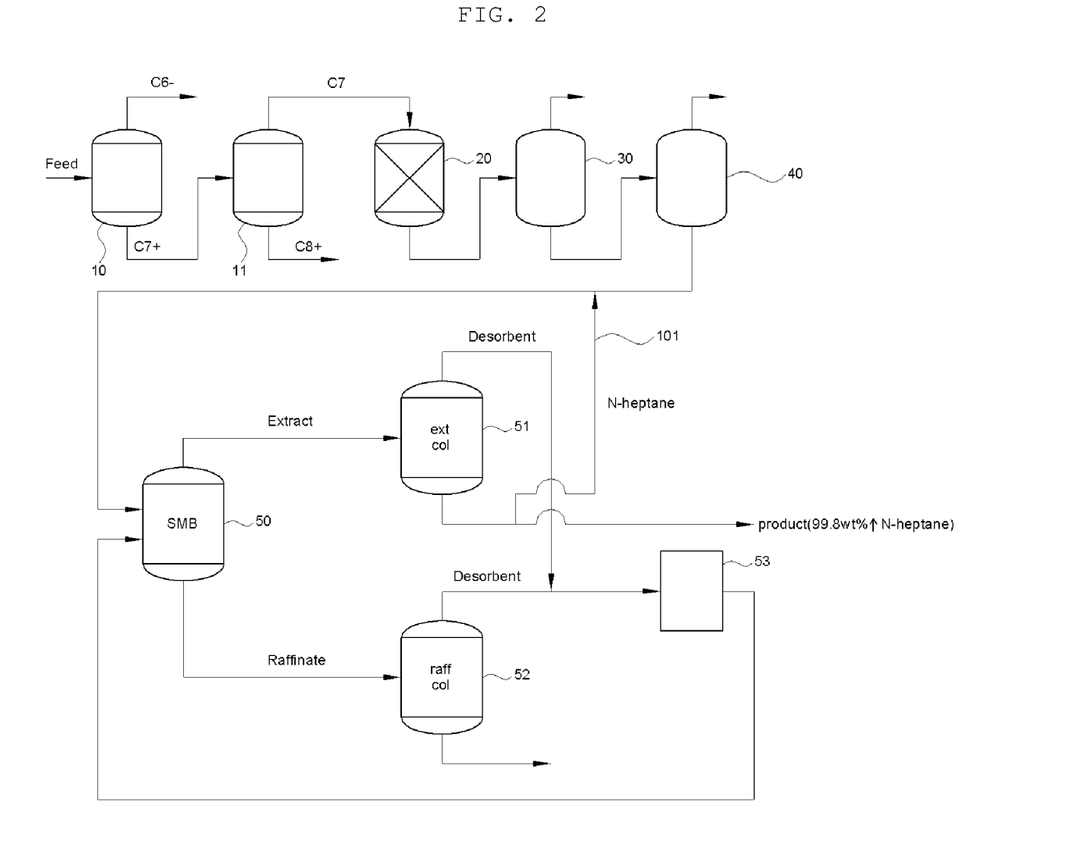
FIG. 2 is a process diagram of an n-heptane production method according to an exemplary embodiment of the present invention.

FIGS. 1 and 2 are process diagrams of the n-heptane production method according to an exemplary embodiment of the present invention.

Hereinafter, the n-heptane production method according to an exemplary embodiment of the present invention will be described with reference to FIGS. 1 and 2.

First, as described in FIG. 1, desulfurized naphtha is added to a first distillation column 10 and the C8+ hydrocarbon component is removed through a lower portion of the first distillation column, and then the C7− hydrocarbon component is separated through an upper portion of the first distillation column.

Thereafter, the C7− hydrocarbon component is added to a second distillation column 11 and the C6− hydrocarbon component is removed through an upper portion of the second distillation column, and then the C7 hydrocarbon component is separated through a lower portion of the second distillation column.

The separated C7 hydrocarbon component is added to a hydrogenation apparatus 20, and unsaturated hydrocarbon components such as an aromatic component and an olefin component are converted into saturated hydrocarbon components by hydrogenation.

Alternatively, as described in FIG. 2, desulfurized naphtha is added to the first distillation column 10 and the C6- hydrocarbon component is removed through the upper portion of the first distillation column, and then the C7+ hydrocarbon component is separated through the lower portion of the first distillation column.

Thereafter, the C7+ hydrocarbon component is added to the second distillation column 11 and the C8+ hydrocarbon component is removed through the lower portion of the second distillation column, and then the C7 hydrocarbon component is separated through the upper portion of the second distillation column.

The separated C7 hydrocarbon component is added to the hydrogenation apparatus 20, and unsaturated hydrocarbon components such as an aromatic component and an olefin component are converted into saturated hydrocarbon components by hydrogenation.

Thereafter, for the hydrogenated discharge, a distillation process by a third distillation column 30 and/or a process of additionally removing a liquid component having a low boiling point through a stripping process by a stripping apparatus 40 may be additionally performed as needed. However, these processes may be additionally performed as needed, and do not necessarily have to be performed in the n-heptane production method according to an exemplary embodiment of the present invention.

Next, the hydrogenated discharge is added to a simulated moving bed (SMB) apparatus 50, n-heptane is separated as an extract through an upper portion of the SMB apparatus, and other components are separated as a raffinate through a lower portion of the SMB apparatus. In this case, a desorbent may be mixed with the extract and the raffinate.

Here, the raffinate may be separated, in a raffinate column 52, into a desorbent (through an upper portion of the raffinate column) and a raffinate (through a lower portion of the raffinate column). The separated raffinate may be used as a raw material in an aromatic component treatment process or may be used as oil for blending gasoline.

The desorbent discharged from the upper portion of the raffinate column may be added to the SMB apparatus 50 again through a desorbent reservoir 53.

The extract discharged from the upper portion of the SMB apparatus 50 contains the separated n-heptane. The extract may be separated, in an extract column 51, into a desorbent (through an upper portion of the extract column) and an extract containing n-heptane (through a lower portion of the extract column).

The desorbent discharged from the upper portion of the extract column may be added to the SMB apparatus 50 again through the desorbent reservoir 53.

The n-heptane discharged from the lower portion of the extract column may be obtained as a final product.

Meanwhile, here, in order to increase the purity of the final n-heptane product to 99.8 wt % or higher, the n-heptane discharged from the lower portion of the extract column 51 may be recirculated between a rear end of the hydrogenation apparatus 20 and a front end of the SMB apparatus 50 through a recirculation pipe 101 connected to a discharge pipe connected to the lower portion of the extract column.

Therefore, as described above, it is possible to produce n-heptane with an ultra-high purity of 99.8 wt % or higher without reduction in the processing capacities in the entire process.

A position at which the n-heptane discharged from the lower portion of the extract column 51 is recirculated is illustrated in FIG. 1 by way of example, the position at which the discharged n-heptane is recirculated is not particularly limited as long as it is located between the rear portion of the hydrogenation apparatus 20 and the front end of the SMB apparatus 50.

Hereinafter, preferred examples and comparative examples of the present invention will be described. However, the following examples are merely preferred examples of the present invention, and the present invention is not limited to the following examples.

Example 1

N-heptane was produced according to a process as illustrated in FIG. 1 by using desulfurized naphtha subjected to a desulfurization process as a raw material. A recirculation rate was 45%, the recirculation rate being obtained by recirculating a discharge liquid containing n-heptane discharged from the extract column to the front end of the SMB apparatus.

Compositions of the desulfurized naphtha used in this case are as shown in Table 1.

TABLE 1

| | C6- n-paraffin | C7 n-paraffin | C8+ n-paraffin | Naph-thene | Iso-paraffin | Aromatic component | Total amount |
|---|---|---|---|---|---|---|---|
| (Content, wt %) | 8.45 | 9.90 | 7.72 | 28.80 | 35.28 | 9.85 | 100 |

The purity of the n-heptane finally obtained was 99.86 wt %.

Example 2

N-heptane was produced in the same manner as that of Example 1, except that the n-heptane was produced according to a process as illustrated in FIG. 2.

The purity of the n-heptane finally obtained was 99.85 wt %.

Example 3

N-heptane was produced by using desulfurized naphtha having the compositions shown in Table 1 as a raw material in the same manner that of Example 1 in the same yield as in Example 1, without recirculation of the discharge liquid containing the n-heptane discharged from the extract column.

The purity of the n-heptane finally obtained was 99.36 wt %.

Comparative Example 1

Figure 3:
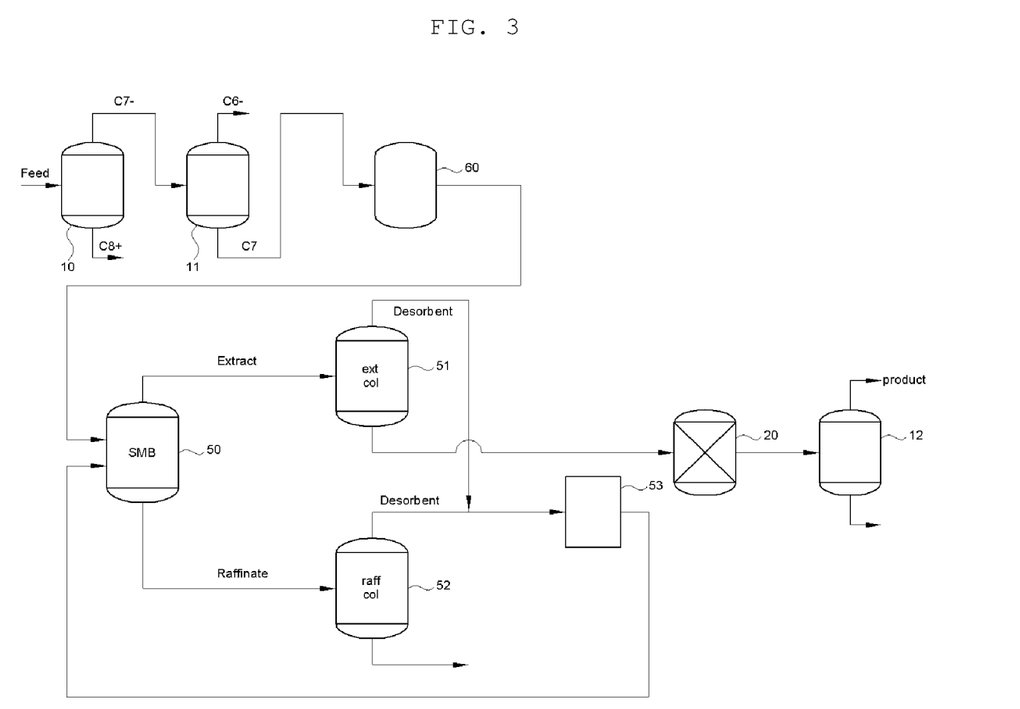
FIG. 3 is a process diagram of an n-heptane production method of Comparative Example 1.

N-heptane was produced according to a process as illustrated in FIG. 3 by using desulfurized naphtha having the compositions shown in Table 1 as a raw material in the same yield as in Example 1.

The purity of the n-heptane finally obtained was 99.51 wt %.

In a case where the SMB process and the hydrogenation process as illustrated in FIG. 3 were performed, in order to produce n-heptane with a purity of 99 wt % or higher, a distillation process 12 was necessarily required at the last stage.

Comparative Example 2

Figure 4:
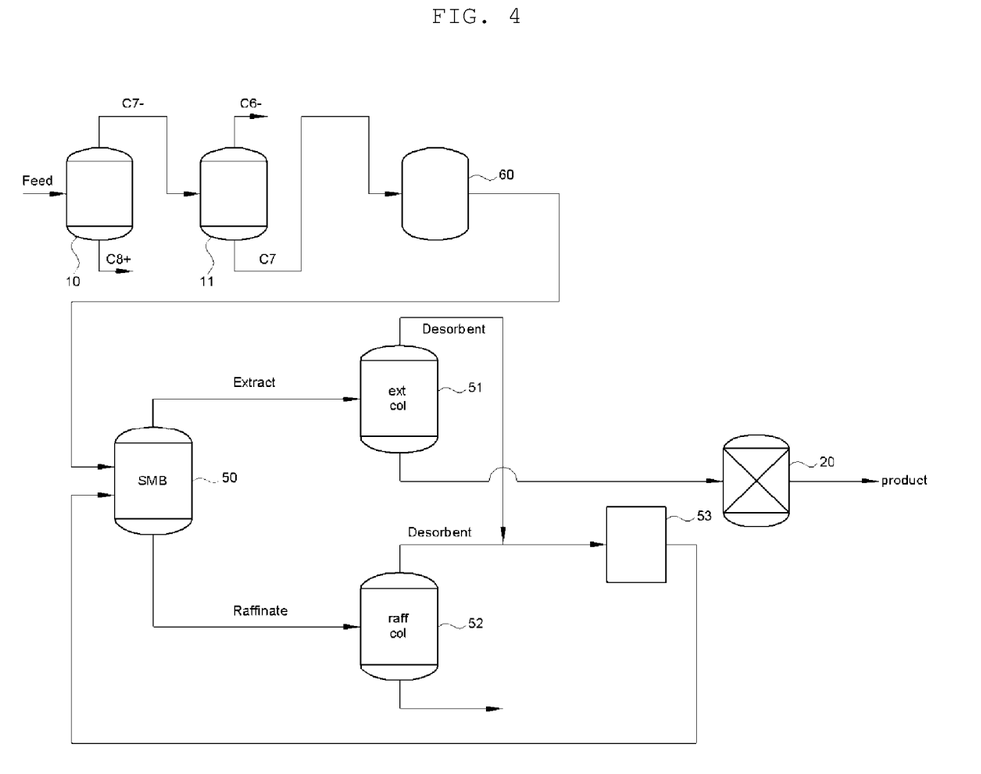
FIG. 4 is a process diagram of an n-heptane production method of Comparative Example 2.

N-heptane was produced according to a process as illustrated in FIG. 4 by using desulfurized naphtha having the compositions shown in Table 1 as a raw material in the same yield as in Example 1.

The purity of the n-heptane finally obtained was 95.12 wt %.

In a case where the SMB process and the hydrogenation process as illustrated in FIG. 4 were performed, when an additional distillation process was not performed at the last stage, n-heptane with a purity of 98 wt % or higher, and more specifically, 99 wt % or higher was not produced.

As set forth above, according to an exemplary embodiment of the present invention, there is provided the n-heptane production method capable of preventing a trade-off between an increase in purity and a decrease in production, while being capable of producing n-heptane with a high purity and furthermore producing n-heptane with an ultra-high purity of 99.8 wt % or higher from desulfurized naphtha.

In addition, according to the n-heptane production method according to an exemplary embodiment of the present invention, an n-heptane product is produced from desulfurized naphtha used as a raw material in an aromatic compound treatment process (BTX process), the profitability in the BTX process may thus be improved. Furthermore, in a case where the desulfurized naphtha from which n-paraffin is removed by the production method of the present invention is used as the raw material in the BTX process, the yield in the BTX process may also be increased.

What is claimed is:

1. An n-heptane production method comprising:
   a step of distilling a feed containing C6–, C7, and C8+ hydrocarbon components, removing the C8+ and C6– hydrocarbon components, and separating the C7 hydrocarbon component;
   a step of adding the separated C7 hydrocarbon component to a hydrogenation apparatus and hydrogenating the separated C7 hydrocarbon component;
   a step of adding the hydrogenated C7 hydrocarbon component to a simulated moving bed (SMB) apparatus and separating the hydrogenated C7 hydrocarbon component into an extract containing n-heptane and a raffinate containing other components;
   a step of distilling the extract and separating the n-heptane in an extract column to obtain a produced n-heptane; and
   a step of recirculating a portion of the n-heptane separated in the extract column between a rear end of the hydrogenation apparatus and a front end of the SMB apparatus,
   wherein, in the recirculation step, a recirculation rate is 30% to 60% by weight of the n-heptane separated;
   wherein a purity of the produced n-heptane is 99.8 wt % or higher.

2. The n-heptane production method of claim 1, wherein the step of distilling the feed containing C6–, C7, and C8+ hydrocarbon components, removing the C8+ and C6– hydrocarbon components, and separating the C7 hydrocarbon component includes:
   a step of performing distillation and removing the C8+ hydrocarbon component in a first distillation column; and
   a step of performing distillation and removing the C6– hydrocarbon component in a second distillation column.

3. The n-heptane production method of claim 1, wherein the step of distilling the feed containing C6–, C7, and C8+ hydrocarbon components, removing the C8+ and C6– hydrocarbon components, and separating the C7 hydrocarbon component includes:
   a step of performing distillation and removing the C6– hydrocarbon component in a first distillation column; and
   a step of performing distillation and removing the C8+ hydrocarbon component in a second distillation column.

4. The n-heptane production method of claim 1, wherein the feed containing C6–, C7, and C8+ hydrocarbon components is desulfurized naphtha.

5. The n-heptane production method of claim 1, wherein the feed containing C6–, C7, and C8+ hydrocarbon components contains, with respect to a total weight of 100 wt % thereof, 3 wt % to 10 wt % of C6– n-paraffin, 5 wt % to 15 wt % of C7 n-paraffin, 5 wt % to 20 wt % of C8+ n-paraffin, and a balance containing naphthene, isoparaffin, and an aromatic component.

* * * * *